US010093892B2

(12) United States Patent
Nishimura et al.

(10) Patent No.: US 10,093,892 B2
(45) Date of Patent: Oct. 9, 2018

(54) ISOLATOR SYSTEM AND DECONTAMINATION METHOD THEREFOR

(71) Applicant: SHIBUYA CORPORATION, Kanazawa-shi, Ishikawa (JP)

(72) Inventors: Tetsuya Nishimura, Kanazawa (JP); Katsuki Hashimoto, Kanazawa (JP); Kazuhito Tanimoto, Kanazawa (JP)

(73) Assignee: SHIBUYA CORPORATION, Kanazawa-shi, Ishikawa (JP)

( * ) Notice: Subject to any disclaimer, the term of this patent is extended or adjusted under 35 U.S.C. 154(b) by 0 days.

(21) Appl. No.: 15/450,344

(22) Filed: Mar. 6, 2017

(65) Prior Publication Data
US 2017/0275581 A1 Sep. 28, 2017

(30) Foreign Application Priority Data
Mar. 24, 2016 (JP) .................................. 2016-060459

(51) Int. Cl.
| | | |
|---|---|---|
| *C12M 1/12* | (2006.01) | |
| *A61L 2/20* | (2006.01) | |
| *C12M 1/00* | (2006.01) | |
| *B01L 1/02* | (2006.01) | |

(52) U.S. Cl.
CPC ............. *C12M 37/00* (2013.01); *A61L 2/208* (2013.01); *C12M 23/06* (2013.01); *C12M 23/58* (2013.01); *C12M 29/00* (2013.01); *C12M 37/04* (2013.01); *C12M 41/14* (2013.01); *C12M 47/16* (2013.01); *A61L 2202/121* (2013.01); *B01L 1/02* (2013.01)

(58) Field of Classification Search
CPC . A61L 2/20; A61L 2/202; A61L 2/206; A61L 2/208; C12M 23/58; C12M 37/00; C12M 37/04; C12M 47/16
See application file for complete search history.

(56) References Cited

U.S. PATENT DOCUMENTS

2012/0183456 A1\* 7/2012 Hirosawa .................. A61L 2/26
422/544

FOREIGN PATENT DOCUMENTS

JP 2015-139421 A 8/2015

\* cited by examiner

*Primary Examiner* — Timothy C Cleveland
(74) *Attorney, Agent, or Firm* — Flynn Thiel, P.C.

(57) ABSTRACT

An isolator system 1 includes: a main isolator 3 in which an aseptic state is maintained and which is for performing an aseptic operation; an incubator 4 in which the aseptic state is maintained and which is connected to the main isolator 3 and is for culturing cells and the like; decontamination means 35 for decontaminating the inside of the main isolator 3; and a decontamination station 9 that decontaminates the inside of the incubator 4. The isolator system 1 further includes a blocking member 30 for sealing a connection port 13 from the outside, the port being provided in the main isolator 3 and being for connection with the incubator 4. When the inside of the main isolator 3 is decontaminated, the connection port 13 is sealed from the outside with the blocking member 30. The isolator system that can efficiently decontaminate the main isolator and the subisolator connected to this main isolator can be provided.

1 Claim, 7 Drawing Sheets

ISOLATOR SYSTEM AND DECONTAMINATION METHOD THEREFOR

FIELD OF THE INVENTION

The present invention relates to an isolator system and a decontamination method therefor, and more specifically, to an isolator system that includes a main isolator for aseptic operations, a subisolator connectable to the main isolator, and decontamination means for decontaminating these isolators, and enables an efficient decontamination operation to be executed in order to construct an aseptic environment, and to a decontamination method therefor.

DESCRIPTION OF THE PRIOR ART

In the regenerative medicine field and pharmaceutical field, isolator systems are used for operations in aseptic environments.

As an isolator system used in the regenerative medicine field, an isolator system has been known that includes a main isolator for performing a required operation necessary for cell culture, and incubators for cell culture serving as subisolators, the subisolator being connected to the main isolator (e.g., Japanese Patent Laid-Open No. 2015-139421).

The isolator system in Japanese Patent Laid-Open No. 2015-139421 includes multiple incubators serving as subisolators, and dedicated decontamination means for decontaminating the insides of the incubators, and is configured so that the insides of the incubators can be decontaminated during operation at the main isolator for the sake of next use.

In the isolator system in the above gazette, the multiple incubators are accommodated in a storage chamber, while the main isolator is provided outside of the storage chamber, the storage chamber being configured to communicate with the inside of the main isolator through an opening. The opening can be closed with a door provided in the main isolator.

Incidentally, in the system in Japanese Patent Laid-Open No. 2015-139421, when the incubator is connected to the main isolator, the incubator is joined to the opening, and the door of the incubator and the door of the main isolator are opened, thus allowing the insides to communicate with each other. When the inside of the main isolator is decontaminated, the insides of the storage chamber and the main isolator are supplied with hydrogen peroxide vapor, which serves as a decontamination medium, in a state where the doors at the opening are opened, thus even allowing covered spots, including sealed portions of the doors at the opening, to be decontaminated.

Such a configuration decontaminates the entire region in the storage chamber, thus decontaminating the covered spots, including the sealed portions at the opening and the door of the main isolator, and the outer surface of the incubator. Consequently, the incubator and the main isolator can be maintained in an aseptic state, and operation is allowed with the insides thereof communicating with each other.

Unfortunately, the system in Japanese Patent Laid-Open No. 2015-139421 has problems in that the entire region in the storage chamber is required to be decontaminated, a large amount of the decontamination medium is required at one time, large decontamination medium supply means is required, and aeration for removing the decontamination medium requires enormous time.

Furthermore, another problem occurs in that in a case of a configuration allowing the subisolators to be connected at multiple spots on the main isolator, decontamination validations (verification) are required in conformity with the number of connected subisolators, initial and periodic validations are required in multiple connection forms, and the validations require many efforts.

SUMMARY OF THE INVENTION

In view of the situations described above, an aspect is an isolator system including a main isolator in which an aseptic operation is performed, and a subisolator connectable to the main isolator, characterized by comprising:

a first opening connector which is formed at the main isolator and through which an item can be loaded and unloaded; a first opening/closing member which opens and closes the first opening connector in the main isolator; a first blocking member which blocks the first opening connector outside of the main isolator; and a first decontamination mechanism which supplies a decontamination medium into the main isolator to perform decontamination;

a second opening connector which is formed at the subisolator and through which the item can be loaded and unloaded; and a second opening and closing member which opens and closes the second opening connector in the subisolator; and connection means for connecting the first opening connector and the second opening connector to each other, and causing an inside of the main isolator and an inside of the subisolator to communicate with each other in a state where inflow of an external atmosphere is blocked, wherein when the inside of the main isolator is decontaminated, the first opening connector is not connected with the second opening connector, and the first opening connector is blocked with the first blocking member from an outside.

A second aspect is a method of decontaminating an isolator system including a main isolator in which an aseptic operation is performed, and a subisolator connectable to the main isolator, characterized in that when an inside of the main isolator is decontaminated, the method disengages connection between a first opening connector formed at the main isolator and a second opening connector formed at the subisolator, blocks the first opening connector with a first blocking member at an outside, opens a first opening/closing member which opens and closes the first opening connector in the main isolator, and supplies a decontamination medium into the main isolator to perform decontamination in this state to decontaminate a covered spot which is not exposed when the first opening/closing member is closed.

Such an isolator system and a decontamination method therefor can provide an isolator system that can efficiently decontaminate the main isolator for an aseptic operation and the subisolator connected to the main isolator.

BRIEF DESCRIPTION OF THE DRAWINGS

FIG. 3(A) shows a state where an inner opening end of the connection port is sealed with a closing member, and FIGS. 3(B) and 3(C) show operation processes of opening the closing member;

FIG. 4(A) shows a state where an inner opening end of the connection port is sealed with a closing member, and FIG. 4(B) shows a state where the closing member is opened;

FIGS. 5(A), 5(B) and 5(C) show processes of connection;

FIG. 6(A) shows a state of being connected to the large connection port, and FIG. 6(B) shows a state of being sealed with a cover member from the outside;

DETAILED DESCRIPTION OF THE EMBODIMENTS

Figure 1:
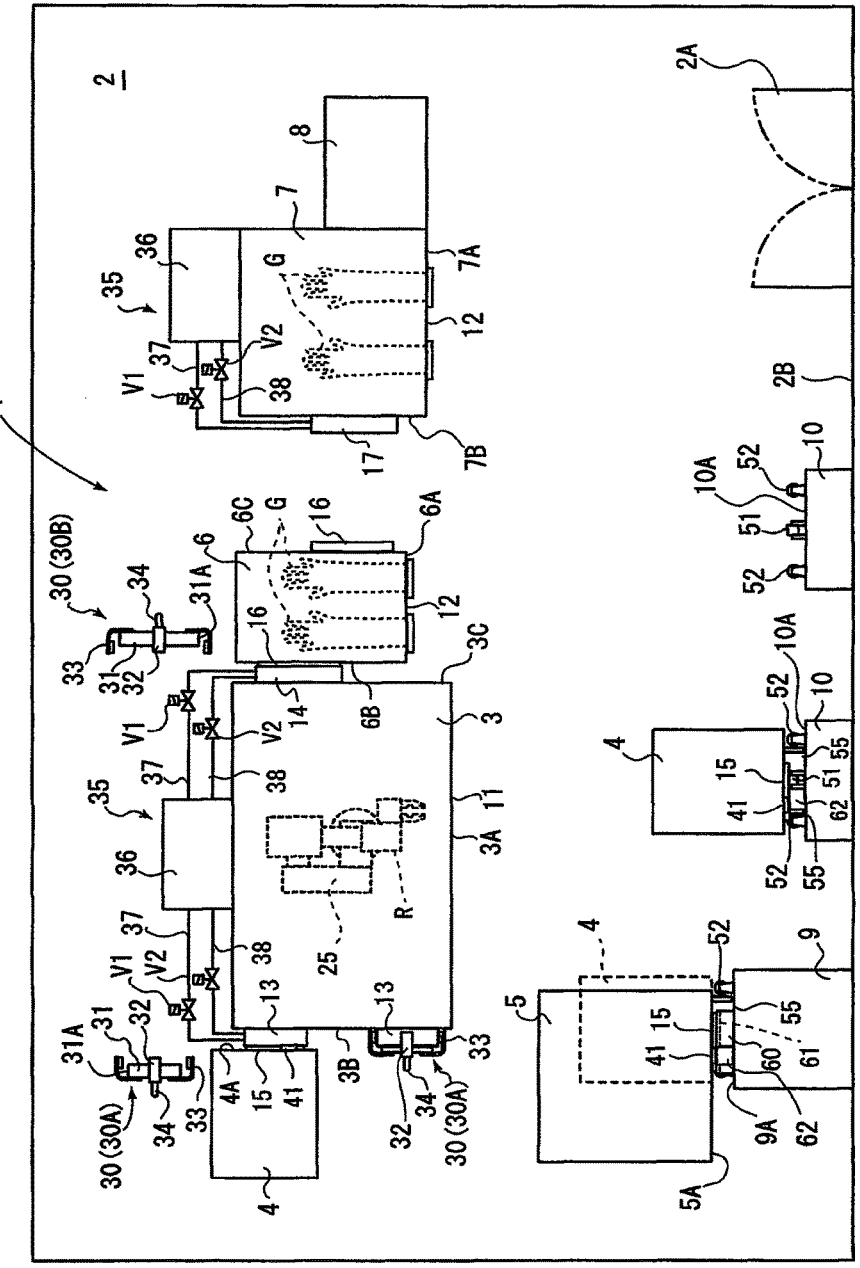
FIG. 1 is a schematic plan view showing an embodiment of the present invention.

The present invention is hereinafter described with reference to illustrated embodiments. Reference numeral 1 in FIG. 1 denotes an isolator system for culturing human cells and tissue. This isolator system 1 is provided in an operation room 2 such as in culturing facilities. At a required time, an operator enters the operation room 2 by opening and closing an open/close door 2A, and performs operations accompanying culture.

The isolator system 1 includes: a main isolator 3 whose inside is maintained to be in an aseptic state and is for performing operations required for culture; small incubators 4 and a large incubator 5 that each serve as subisolators whose insides are maintained to be in the aseptic state, are connected to the main isolator 3, and are for culturing cells and tissue; a material introduction module 6 that serves as a subisolator whose inside is maintained to be in the aseptic state, is connected to the main isolator 3, and is for allowing items to be introduced into the main isolator 3; a manual operation module 7 that serves as an attachment isolator whose inside is maintained to be in the aseptic state, and allows the material introduction module 6 to be connected; and a pass box 8 provided serially to the manual operation module 7. This system further includes: a decontamination station 9 for decontaminating the incubators 4 and 5 and for executing culture for the large incubator 5; and culture stations 10 for executing culture for the small incubator 4.

This embodiment is provided with two small incubators 4 and two culture stations 10. Alternatively, the numbers of incubators and stations may be increased or reduced as required.

Figure 2:
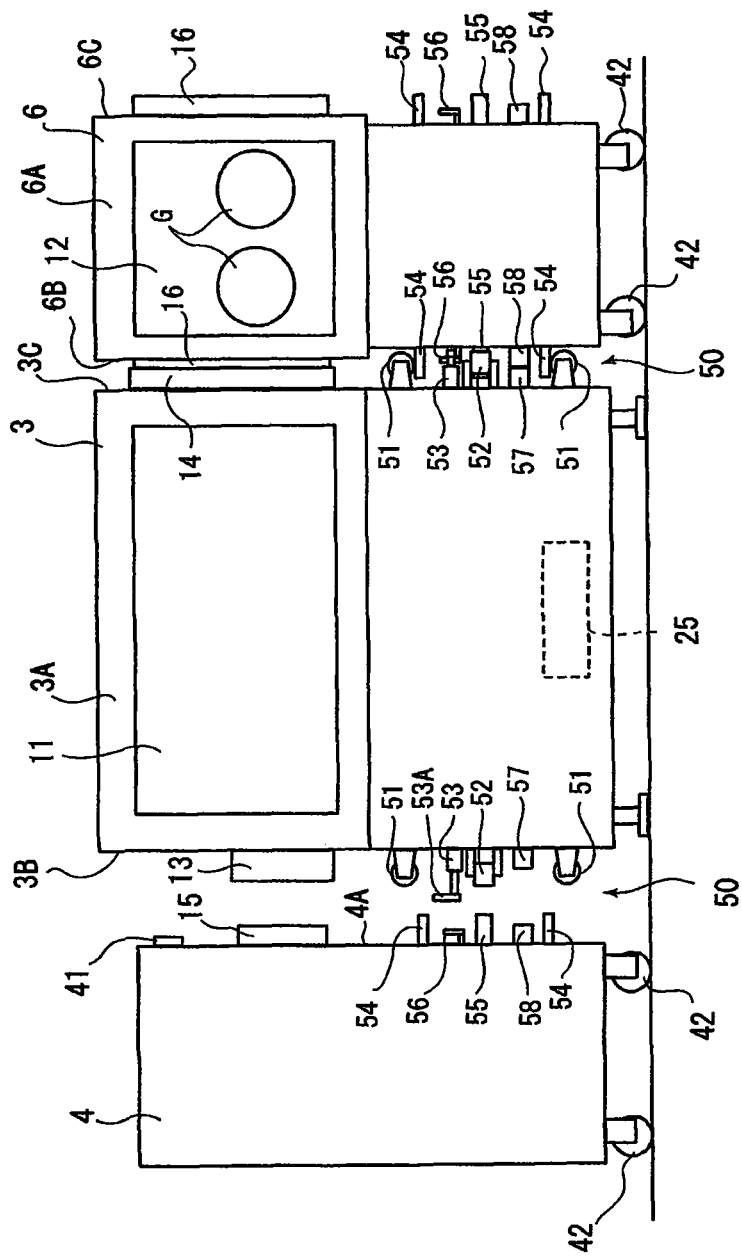
FIG. 2 is a front view showing a state of using a main isolator and a subisolator.

The main isolator 3 is fixedly arranged at a predetermined position in the operation room 2. As shown in FIG. 2, a transparent window 11 is provided on a front surface 3A of the main isolator 3. In the main isolator 3, operations required for culture are performed by a robot R. Furthermore, a front surface 6A of the material introduction module 6 is also provided with a transparent window 12. This window 12 is provided with a glove G for allowing the operator to insert a hand for manual operation. Likewise, a front surface 7A of the manual operation module 7 is also provided with a transparent window 12 that includes a glove G.

On one side surface 3B of the main isolator 3, a small connection port 13 is formed. On the other side surface 3C, a large connection port 14 is formed. The one connection port 13 of the main isolator 3 can be connected with each of small connectors 15 formed on front surfaces 4A and 5A of the respective incubators 4 and 5. The other connection port 14 can be connected with a large connector 16 formed on one side surface 6B of the material introduction module 6. On a side surface 7B of the manual operation module 7, a large connection port 17 that is similar to the large connection port 14 is formed, and can be connected with the large connector 16 formed on the other side surface 6C of the material introduction module 6.

Through adjustment of supply and exhaust rates, the insides of the main isolator 3, the incubators 4 and 5 and the material introduction module 6 as the subisolators, and manual operation module 7 as the attachment isolator are maintained to have a positive pressure that is higher than that in the operation room 2, which prevents outside air from flowing thereinto, and maintains the aseptic state after decontamination.

In this embodiment, the two connection ports 13 are juxtaposed to each other on the side surface 3B of the main isolator 3.

Figure 3A:
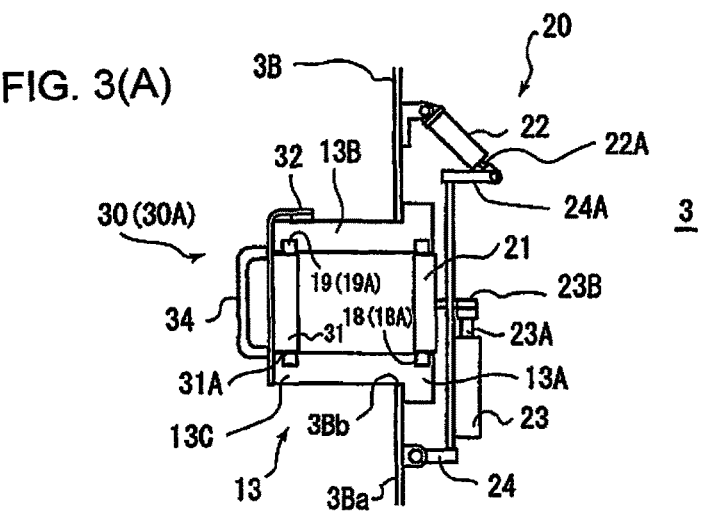
FIGS. 3(A), 3(B) and 3(C) are sectional views showing a small connection port in a state of being sealed from the outside with a small blocking member.

As shown in FIG. 3(A), the small connection port 13 includes a tubular member 13B that has a rectangular tubular shape and includes an inner opening end 13A disposed inside of the main isolator 3 having a flanged shape. The connection port 13 is fitted onto a substantially rectangular opening 3Bb from the inner side of the main isolator 3 in a state where the hermeticity is held; the opening 3Bb is formed on a side wall 3Ba that constitutes the side surface 3B of the main isolator 3. Such opening 3Bb and connection port 13 constitute a first opening connector that allows an item, such as a culture vessel in which cells have been planted, to be loaded and unloaded.

Annular tube seal means 18 is implanted on the inner peripheral surface of the inner opening end 13A having a flanged shape at one end of the connection port 13. Likewise, similar annular tube seal means 19 is also implanted on the inner peripheral surface of an outer opening end 13C at the other end. The pieces of annular tube seal means 18 and 19 constitute seal means for inflating annular tubes 18A and 19A by supplying air to seal a gap caused when the inner and outer opening ends 13A and 13C are closed.

Figure 4A:
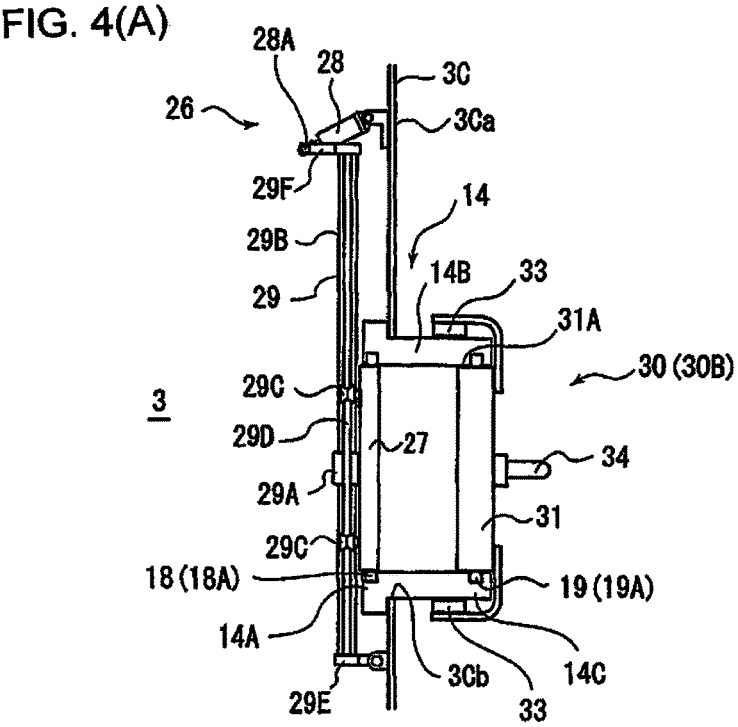
FIGS. 4(A) and 4(B) are sectional views showing a large connection port in a state of being sealed from the outside with a large blocking member.

The configuration of the connection port 13 is common to the configurations of the large connection ports 14 and 17. As shown in FIG. 4(A), at the connection port 14, a tubular member 14B is fitted to a substantially rectangular opening 3Cb formed on a side wall 3Ca with an inner opening end 14A being positioned on the inner side of the isolator 3; the side wall 3Ca constitutes the side surface 3C of the main isolator 3. Such opening 3Cb and connection port 14 constitute the first opening connector through which items, such as materials, can be loaded and unloaded.

On the inner surface of the one side wall 3Ba of the main isolator 3, an inner opening/closing mechanism 20 that opens and closes the inner opening end 13A of the connection port 13 is provided. A closing member 21 provided for the inner opening/closing mechanism 20 is attached and detached to and from the inner opening end 13A, thereby allowing the inner opening end 13A to be opened and closed.

The closing member 21 has a substantially rectangular external shape that is slightly smaller than and geometrically similar to that of the inner opening end 13A having a substantially rectangular opening shape. In a state where the closing member 21 is fitted to the inner opening end 13A, a gap is formed between this member and the inner surface of the inner opening end 13A. In this state, the annular tube 18A of the annular tube seal means 18 is inflated to be in close contact with an outer peripheral surface 21A of the closing member 21 shown in FIGS. 3(B) and 3(C), thereby sealing the gap. As shown in FIG. 4(A), on the inner surface of the other side wall 3Ca of the main isolator 3 is provided with an inner opening/closing mechanism 26 that opens and closes the inner opening end 14A of the connection port 14. The inner opening end 14A is opened and closed by a closing member 27. Such closing members 21 and 27 constitute a first opening/closing member that opens and closes the first connection opening in the main isolator 3.

As shown in FIG. 3(A), the inner opening/closing mechanism 20 includes upper swing drive means 22 and lower opening/closing drive means 23 that are made up of electric cylinders and are attached to the inner surface of the side wall 3Ba of the main isolator 3 swingably in the upward and downward directions.

The closing member 21 is joined to the distal end of a drive rod 23A of the opening/closing drive means 23 via a bracket 23B. The opening/closing drive means 23 is fixed to the long side of the L-shape of an L-shaped bracket 24 provided on the side wall 3Ba swingably in the upward and downward directions. The distal end of the short side of the L-shape is swingable on the side wall 3Ba. The distal end of a drive rod 22A of the swing drive means 22 is rotatably joined to a joining member 24A provided on the distal end of the long side of the L-shape.

Figure 3B:
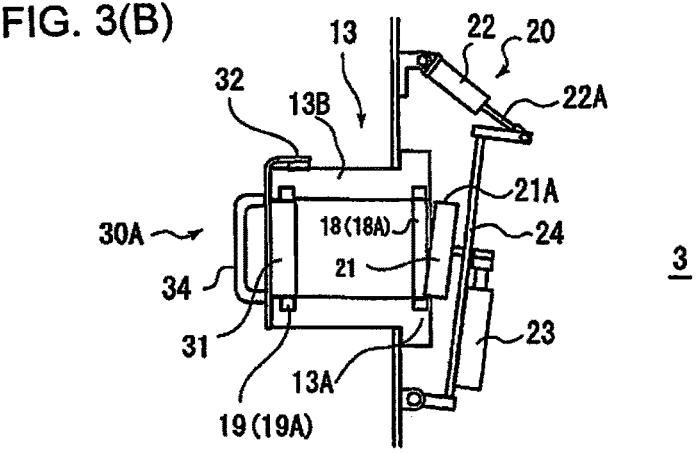
Figure 3C:
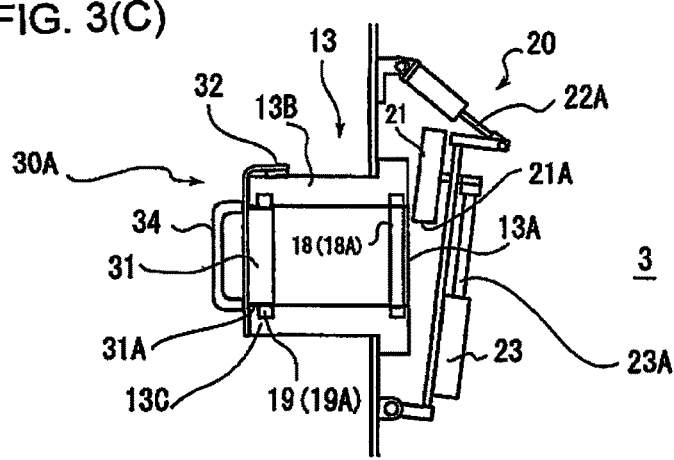

The operations of the swing drive means 22 and the opening/closing drive means 23 are controlled by control means 25 that is provided in the main isolator 3 and shown in FIG. 2. When the closed inner opening end 13A of the connection port 13 shown in FIG. 3(A) is opened, the annular tube 18A is deflated by exhausting air, and subsequently, the swing drive means 22 shown in FIG. 3(B) is actuated to elongate the retracted drive rod 22A as shown in FIG. 3(B), thereby including the opening/closing drive means 23 together with the L-shaped bracket 24 toward the inside of the main isolator 3. Accordingly, the upper portion of the closing member 21 is separated from the inner opening end 13A of the connection port 13. From this state, the opening/closing drive means 23 is actuated as shown in FIG. 3(C) to elongate the retracted drive rod 23A and move the closing member 21 obliquely upward from the inner opening end 13A. The inner opening end 13A of the connection port 13 can thus be opened. When the end is closed, an operation opposite from this operation is performed.

As shown in FIG. 4(A), at the large connection port 14, the inner opening/closing mechanism 26 moves the closing member 27 in a lateral direction, and includes swing drive means 28 made up of an electric cylinder, and opening/closing drive means 29 made up of a linear motion actuator. Each piece of the means is swingably attached to the inner surface of the side wall 3Ca of the main isolator 3 with the connection port 14 being interposed therebetween.

A movable member 29A of the opening/closing drive means 29 is joined to a lower portion of the closing member 27, which is moved in the lateral direction along a guide 29B disposed frontward on the lower side of the closing member 27. At two upper spots on the closing member 27, guide rollers 29C are provided, and are guided in the lateral direction by a guide rod 29D disposed frontward on the upper side of the closing member 27. The guide 29B and the guide rod 29D are joined to each other by a joining member 29E on one end side and swingably supported on the side wall 3Ca, are joined to each other on the other end side by a joining member 29F, and are joined to the distal end of a drive rod 28A of the swing drive means 28 in a rotatable state.

Figure 4B:
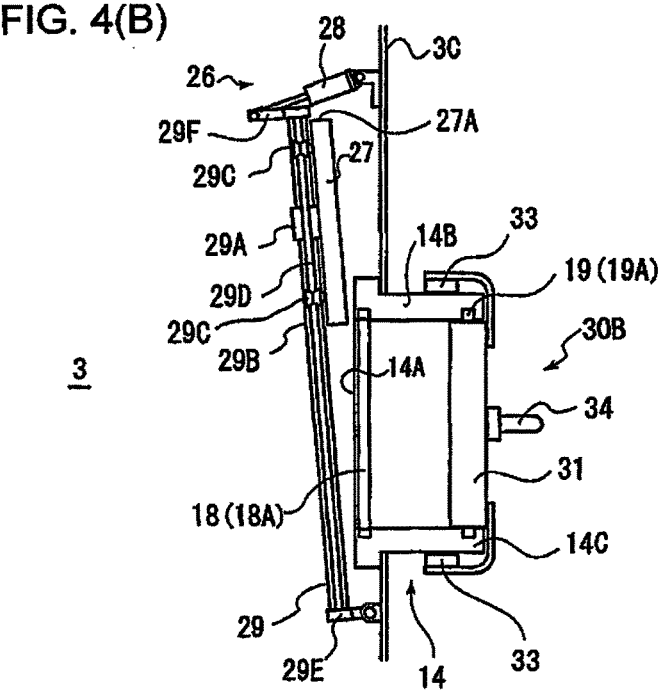

According to such a configuration, in the state where the closing member 27 is closed as shown in FIG. 4(A), the annular tube 18A of the annular tube seal means 18 is deflated, and the drive rod 28A of the swing drive means 28 is elongated, thereby pushing the opening/closing drive means 29 about a pivot on the joining member 29E side toward the inside of the main isolator 3. In this state, the movable member 29A of the opening/closing drive means 29 is moved to the distal end side joined to the swing drive means 28, thereby allowing the closing member 27 to be separated from the inner opening end 14A to open the connection port 14, as shown in FIG. 4(B). The operation of the inner opening/closing mechanism 26 is also controlled by the control means 25.

Likewise, the large connection port 17 provided for the manual operation module 7 is also provided with the similar inner opening/closing mechanism 26, and is opened and closed by the closing member 27.

As shown in FIGS. 1, 3(A), 3(B), 3(C), 4(A) and 4(B), the isolator system 1 further includes blocking members 30 serving as first blocking members that block the outer opening ends 13C and 14C of the small connection port 13 and the large connection port 14 at their outsides.

The blocking members 30 include a small blocking member 30A corresponding to the small connection port 13 shown in FIGS. 3(A), 3(B) and 3(C), and a large blocking member 30B corresponding to the large connection port 14 shown in FIGS. 4(A) and 4(B). As with the closing member 21, these members include: fitting members 31 that have substantially rectangular external shapes that are slightly smaller than and geometrically similar to those of the outer opening ends 13C and 14C having substantially rectangular opening shapes; upper pieces 32 that are engaged with the upper outer peripheral surfaces of the tubular members 13B and 14B of the connection ports 13 and 14; dual-side pieces 33 that clamp the outer peripheral surfaces of the tubular members 13B and 14B on both sides; and handles 34.

In the state where the fitting members 31 are fitted to the outer opening ends 13C and 14C of the connection ports 13 and 14, slight gaps are formed between outer peripheral surfaces 31A of the fitting members 31 and the inner peripheral surfaces of the outer opening ends 13C and 14C. In this state, the annular tubes 19A of the annular tube seal means 19 on the outer opening ends 13C and 14C sides are inflated, thereby sealing the outer opening ends 13C and 14C. These small blocking member 30A and large blocking member 30B are prepared in conformity with the number of connection ports 13 and 14.

As shown in FIG. 1, decontamination means 35 that is provided for the main isolator 3 and serves as a first decontamination mechanism includes: a supply and exhaust source 36 of a decontamination medium; and a supply pipe 37 and an exhaust pipe 38 that connect the connection ports 13 and 14 and the supply and exhaust source 36 to each other. At the midways of the supply pipe 37 and the exhaust pipe 38, electromagnetic open/close valves V1 and V2 that are normally closed are provided. The operations of these valves are controlled by the control means 25. Such decontamination means 35 supplies hydrogen peroxide vapor as a decontamination medium from the supply and exhaust source 36 into the main isolator 3, circulates the vapor, and further removes a decontamination component through aeration. Furthermore, this means supplies the decontamination medium (hydrogen peroxide vapor) through the supply pipe 37 to the connection ports 13 and 14, and exhausts the medium through the exhaust pipe 38, thus circulating the medium. Moreover, this means aerates the connection ports 13 and 14 through the supply pipe 37 and the exhaust pipe 38, thereby allowing the decontamination component to be removed.

Such decontamination means 35 is also provided for the manual operation module 7 that includes the large connection port 17. As to the manual operation module 7, the inside of the material introduction module 6 connected to the manual operation module 7 through the pass box 8 and the connection port 17 is decontaminated by the decontamination means 35, and the decontamination medium is supplied into the connection port 17 using the supply pipe 37 and the exhaust pipe 38 as with the connection ports 13 and 14. Thus, the decontamination means 35 provided for the manual operation module 7 is for decontamination through supplying the decontamination medium into the material introduction module 6 serving as the subisolator, and constitutes a second decontamination mechanism.

As shown in FIGS. 1 and 2, on a front surface 4A of the small incubator 4 and a front surface 5A of the large incubator 5, the respective small connectors 15 are provided. The connectors 15 constitute second connection openings through which items, such as culture vessels where cells have been planted, can be loaded and unloaded to and from the incubators 4 and 5. On the front surfaces 4A and 5A, a connection pipe 41 is disposed above the connector 15 with an end of this pipe protruding. The path of the connection pipe 41 can be opened and closed by a butterfly valve, not shown, provided in this pipe.

Casters 42 are attached to each of the incubators 4 and 5 at four spots on the bottom. The operator can easily move the incubators 4 and 5 by pushing the incubators. Suspensions are embedded in the casters 42, thereby allowing an error in the height direction to be accommodated when the connector 15 is connected to the connection port 13 of the main isolator 3.

Figure 5A:
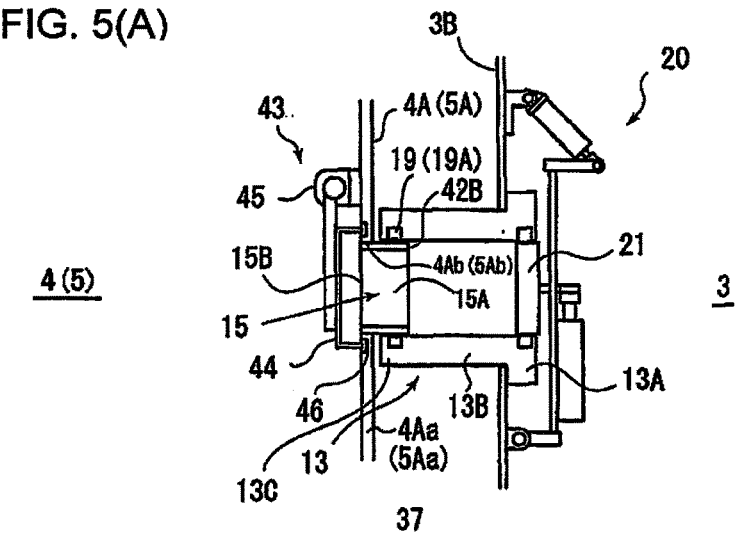
FIGS. 5(A), 5(B) and 5(C) are sectional views showing states where a small connector is connected to the small connection port.

As shown in FIG. 5(A), the connector 15 is made up of a pipe-shaped member 15A that has a rectangular tubular shape and is hermetically fitted to a substantially rectangular opening 4Ab (5Ab) formed on a side wall 4Aa (5Aa) constituting the front surface 4A (5A) of the incubator 4 (5). The pipe-shaped member 15A is formed to have an external shape that is a substantially rectangular and geometrically similar shape slightly smaller than the shape of the inner hollow portion of the tubular member 13B at the small connection port 13 of the main isolator 3, and can be fitted to the inside of the outer opening end 13C of the tubular member 13B. In such a fitted state, a slight gap is formed between the outer peripheral surface of the pipe-shaped member 15A and the inner peripheral surface of the tubular member 13B. This gap is sealed by inflating the annular tube 19A of the annular tube seal means 19 on the outer opening end 13C side. The connector 15 of the incubator 4 (5) can be securely connected to the connection port 13 of the main isolator 3 while blocking the inflow of the external atmosphere. The tubular member 13B (outer tubular member), pipe-shaped member 15A (inner tubular member) and annular tube seal means 19 constitute connection means for connecting the first opening connector and the second opening connector to each other.

The connector 15 can block the incubator 4 (5) at the inside by an inner closing mechanism 43. The inner closing mechanism 43 includes: a lid member 44 serving as a second opening and closing member that opens and closes an inner opening end 15B of the connector 15 in the incubator 4(5); rotation drive means 45 made up of an electric cylinder for opening and closing the lid member 44; and a seal member 46 implanted to surround the periphery of the rectangular inner opening end 15B. This mechanism opens and closes the lid member 44 by actuating the rotation drive means 45. In a closed state, the lid member 44 is pressed against the seal member 46 by the rotation drive means 45, thereby sealing the inner opening end 15B.

As shown in FIGS. 1 and 2, on the side surfaces 6B and 6C of the material introduction module 6, the large connectors 16 are provided. The connectors 16 constitute the second connection openings that allow items including cells and a culture vessel, and culture instruments to be loaded and unloaded to and from the material introduction module 6.

Figure 6A:
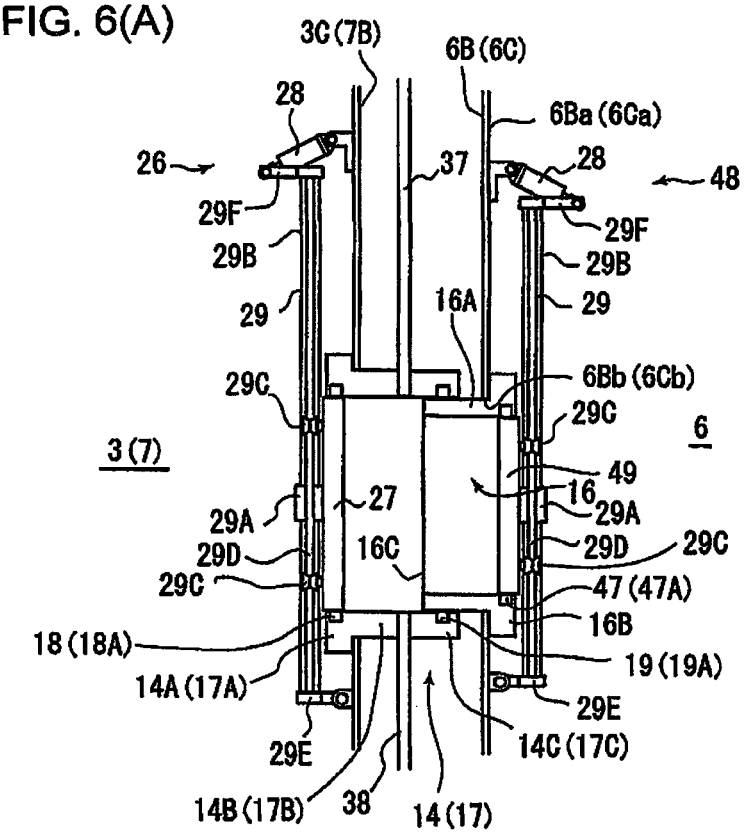
FIGS. 6(A) and 6(B) are sectional views showing a large connector.

As shown in FIG. 6(A), the connector 16 is made up of a pipe-shaped member 16A that has a rectangular tubular shape and is hermetically fitted to a substantially rectangular opening 6Bb (6Cb) formed on a side wall 6Ba (6Ca) constituting the side surface 6B (6C) of the material introduction module 6. The connector 16 is formed to have an outer shape that is a substantially rectangular shape slightly smaller than and geometrically similar to the sectional shapes of the large connection port 14 of the main isolator 3 and the connection port 17 of the manual operation module 7. On the inner peripheral surface of an inner opening end 16B that opens at the inside of the material introduction module 6, annular tube seal means 47 similar to the annular tube seal means 18 and 19 is implanted. The inner opening end 16B is opened and closed by a fitting lid member 49 provided for the inner closing mechanism 48, as a second opening/closing member. The shape of the inner hollow portion of the fitting lid member 49 has an outer shape that is slightly smaller than and geometrically similar to the substantially rectangular inner opening end 16B. In a state of being fitted to the inner opening end 16B, a slight gap is formed. In a state where the fitting lid member 49 is fitted to the inner opening end 16B, an annular tube 47A of the annular tube seal means 47 is inflated, thereby allowing the inner opening end 16B to be sealed. The configuration of the inner closing mechanism 48 that opens and closes the fitting lid member 49 is common to the configurations of the inner closing mechanism 26 for opening and closing the large connection ports 14 and 17. The description thereof is omitted here.

The pipe-shaped member 16A of the connector 16 is to be fitted to the inside of the outer opening end 14C (17C) of the tubular member 14B (17B) of the connection port 14 (17). In such a fitted state, as with the case of the connection port 13 and the connector 15, a slight gap is formed between the tubular member 14B (17B) and the pipe-shaped member 16A. This gap is sealed by inflating the annular tube 19A of the annular tube seal means 19 on the outer opening end 14C (17C) side, thereby allowing the connector 16 to be connected to the connection port 14 (17).

These tubular members 14B and 17B (outer tubular members), pipe-shaped member 16A (inner tubular member) and annular tube seal means 19 constitute connection means for connecting the first opening connector and the second opening connector to each other.

As shown in FIG. 2, for the sake of easily aligning one of the connectors 15 of the movable incubators 4 and 5, and the connector 16 of the material introduction module 6 with the connection port 13 or 14 of the position-fixed main isolator 3 or the connection port 17 of the position-fixed manual operation module 7 and then connecting the connector to the connection port, this embodiment includes positioning mechanisms 50 on opposite surfaces which are the side surfaces 3B and 3C below the connection ports 13 and 14 of the main isolator 3 or the side surface 7B below the connection port 17 of the manual operation module 7 and the front surfaces 4A and 5A below the connectors 15 of the incubators 4 and 5 and the side surfaces 6B and 6C below the connector 16 of the material introduction module 6.

The configurations of the positioning mechanisms 50 are common to each other. The positioning mechanisms 50 provided on the side surface 3B of the main isolator 3 and the front surface 4A of the incubator 4 are hereinafter described.

That is, on the side surface 3B of the main isolator 3, a vertically arranged pair of rotating rollers 51 and a horizontally arranged pair of rotating rollers 52 are provided in a protruding manner. At a predetermined position within the vertical range of the vertical rotating rollers 51 and the horizontal range of the horizontal rotating rollers 52, retracting means 53 that includes an L-shaped movable hook 53A is provided. Meanwhile, on the front surface 4A of the incubator 4, a vertically arranged pair of fitting pieces 54 and a horizontally arranged pair of fitting pieces 55 are provided in a protruding manner. Furthermore, at a predetermined position within the vertical range of the vertical fitting pieces 54 and the horizontal range of the horizontal fitting pieces 55, L-shaped fittings 56 are fixed in a protruding manner.

The vertically arranged pair of rotating rollers 51 is arranged so that the rotating axis can be horizontal. The horizontally arranged pair of rotating rollers 52 is arranged so that the rotating axis is vertically oriented.

As to the positional relationship between the vertically arranged pair of fitting pieces 54 and the vertically arranged pair of rotating rollers 51, the positions in the horizontal direction are substantially identical to each other when the connector 15 of the incubator 4 approaches the connection port 13 of the main isolator 3 for connection. The positions in the vertical direction are defined so that the upper fitting piece 54 can be in contact with the lower part of the upper rotating roller 51 to rotate the rotating roller 51, and the lower fitting piece 54 can be in contact with the upper part of the lower rotating roller 51 to rotate the rotating roller 51. Thus, the vertically arranged pair of fitting pieces 54 are introduced between the vertically arranged pair of rotating rollers 51, and the vertical position of the connector 15 of the incubator 4 is adjusted to that of the connection port 13 of the main isolator.

As to the positional relationship between the horizontally arranged pair of vertical fitting pieces 55 and the horizontally arranged pair of rotating rollers 52, the positions in the vertical direction are substantially identical to each other when the connector 15 of the incubator 4 approaches the connection port 13 of the main isolator 3 for connection. The positions in the horizontal direction are defined so that the left vertical fitting piece 55 with respect to the front surface 4A of the incubator 4 can be in contact with the left side of the right rotating roller 52 with respect to the side surface 3B of the main isolator 3 to rotate the rotating roller 52, and the right vertical fitting piece 55 with respect to the front surface 4A of the incubator 4 can be in contact with the right side of the left rotating roller 52 with respect to the side surface 3B of the main isolator 3 to rotate the rotating roller 52. Thus, the horizontally arranged pair of fitting pieces 55 is introduced between the horizontally arranged pair of rotating rollers 52, and the horizontal position of the connector 15 of the incubator 4 is adjusted to that of the connection port 13 of the main isolator 3. To allow vertical and horizontal alignment, each caster 42 provided for the incubator 4 may be a suspension-implemented caster.

The positional relationship between the L-shaped movable hook 53A and the L-shaped fitting 56 is arranged adjacent to each other in the lateral direction in a case where the connector 15 of the incubator 4 is connected to the connection port 13 of the main isolator 3. When the L-shaped movable hook 53A is rotated about the horizontal shaft by the retracting means 53, the hook is engaged with the L-shaped fitting 56. Furthermore, in this state, retraction in the direction toward the main isolator 3 allows alignment by the vertically arranged pair of fitting pieces 54 and the vertically arranged pair rotating rollers 51 and by the horizontally arranged pair of fitting pieces 55 and the horizontally arranged pair of rotating rollers 52. The connector 15 of the incubator 4 and the connection port 13 of the main isolator 3 shown in FIG. 5(A) are brought into a connectable state. In this state, the annular tube 19A of the annular tube seal means 19 is inflated to seal the gap between the connection port 13 and the connector 15 and to be brought into a connected state.

Besides the positioning mechanism 50, as with the installation position of the retracting means 53, at a predetermined position within the vertical range of the vertical rotating rollers 51 and the horizontal range of the horizontal rotating rollers 52 on the side surfaces 3B and 3C of the main isolator 3 and the side surface 7B of the manual operation module 7, a utility connector 57 is provided that supplies the incubator 4, 5 with carbon dioxide gas, oxygen and aseptic air required for culturing and supplies the incubator 4, 5 and the material introduction module 6 with electric power. Meanwhile, as with the installation position of the L-shaped fitting 56, at a predetermined position within the vertical range of the vertical fitting pieces 54 and the horizontal range of the horizontal fitting pieces 55 on each of the front surfaces 4A and 5A of the incubators 4 and 5 and the side surfaces 6B and 6C of the material introduction module 6, connection targets 58 are provided. These utility connector 57 and connection targets 58 are positioned by the positioning mechanism 50, and are connected at the same time when the connectors 15 and 16 are connected to the connection ports 13, 14 and 17, thereby required air and power are supplied to the incubators 4 and 5 and the material introduction module 6.

Figure 7:
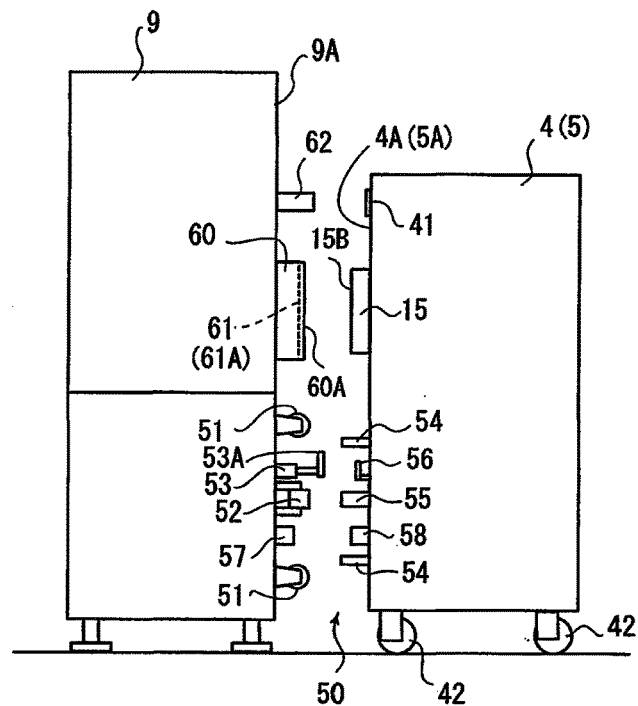
FIG. 7 shows a side view showing a decontamination station and an incubator.

A shown in FIG. 1, the decontamination station 9 is provided along a wall surface 2B of the operation room 2, and installed so that a front surface 9A can face the main isolator 3 and the position can be fixed. As shown in FIG. 7, on the front surface 9A, a fixation cover member 60 serving as a second blocking member for closing the connector 15 of the incubators 4, 5 from the outside is provided at the same position in height as that of the connection port 13 of the main isolator 3. Below this position, the vertically arranged pair of rotating rollers 51, the horizontally arranged pair of rotating rollers 52, the retracting means 53 and the utility connector 57, which constitute the positioning mechanism 50, are provided in the same positional relationship as that in the case of the main isolator 3.

The fixation cover member 60 is made up of a tubular member having the same dimensions and shape as the small connection port 13 of the main isolator 3, and can be connected with the connector 15 of the incubator 4, 5. On the inner peripheral surface of an opening end 60A of the fixation cover member 60, an annular tube 61A of annular tube seal means 61 that is similar to the annular tube seal means 19 is implemented. Unlike the connection port 13, the fixation cover member 60 does not have a penetrated inner structure. This member is formed to have a backward tapered tubular body having a bottom instead. The connector 15 is fitted to the fixation cover member 60 for sealing with the annular tube seal means 61, thus sealing the external opening end 15B of the connector 15.

In such a decontamination station 9, as with the case of connection to the connection port 13 of the main isolator 3, the connector 15 of the incubators 4, 5 can be connected to the fixation cover member 60 by the positioning mechanism 50.

Above the fixation cover member 60, a supply and exhaust pipe 62 connectable to the connection pipes 41, which protrude from each of the front surfaces 4A and 5A of the incubators 4 and 5, is provided. At the same time when the connector 15 is connected to the fixation cover member 60, the connection pipe 41 and the supply and exhaust pipe 62 are connected to each other. Through the supply and exhaust pipe 62, hydrogen peroxide vapor as the decontamination medium is supplied and exhausted to and from any of the insides of the incubators 4, 5, and aeration is further performed, thus performing decontamination.

Furthermore, the decontamination station 9 also functions as a culture station. In a state of connection with the incubators 4, 5 by the positioning mechanism 50, the utility connector 57 of the decontamination station 9 is connected to the connection target 58 of the incubators 4, 5. Through this connection, air and power required for culturing are supplied, which can culture the cells accommodated in the incubators 4, 5 for a predetermined period. In this embodiment, mainly in the large incubator 5, culturing is performed in the decontamination station 9.

Figure 8:
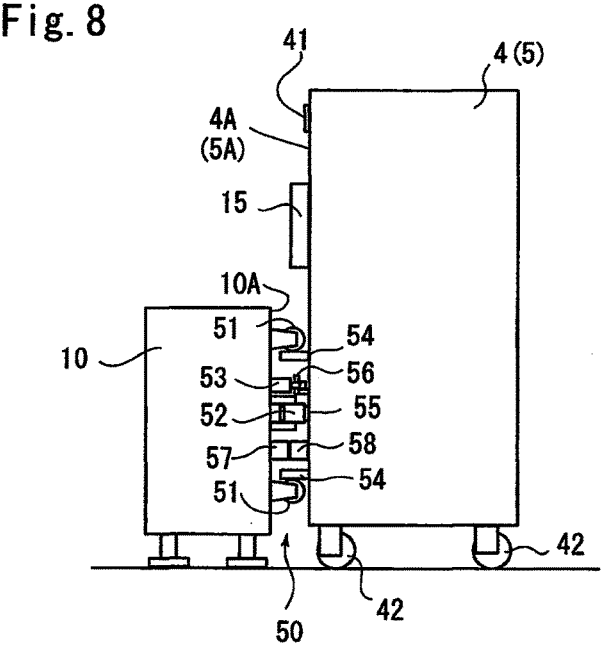
FIG. 8 shows a side view showing a culture station and the incubator.

As shown in FIG. 1, the culture station 10 is provided along a wall surface 2B of the operation room 2 and juxtaposed to the decontamination station 9, and installed so that a front surface 10A can face the main isolator 3 and the position can be fixed. As shown in FIG. 8, on the front surface 10A, the vertically arranged pair of rotating rollers 51, the horizontally arranged pair rotating rollers 52, the retracting means 53, and the utility connector 57, which constitute the positioning mechanism 50, are provided at the same positional relationship as that in the cases of the main isolator 3 and the decontamination station 9.

Thus, in a state of connection with the incubators 4, 5 by the positioning mechanism 50, the utility connector 57 of the culture station 10 is connected to any of the connection targets 58 of the incubators 4, 5. Through this connection, air and power required for culturing are supplied, which can culture the cells accommodated in the incubator 4, 5 for a predetermined period. In this embodiment, two culture stations 10 are juxtaposed to each other. Mainly in the small incubator 4, culturing is performed.

Figure 6B:
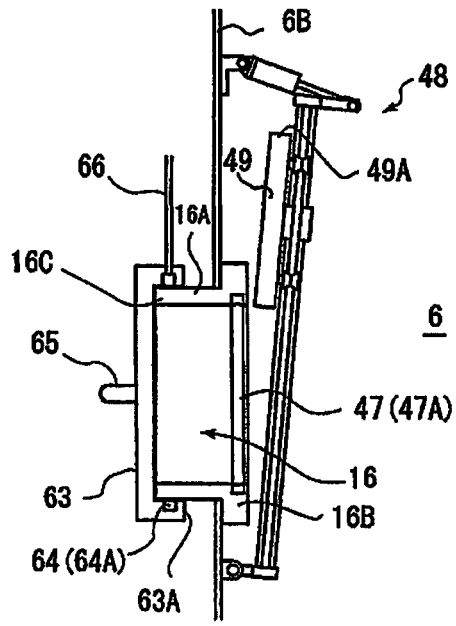

As shown in FIG. 6(B), for the connector 16 of the material introduction module 6, a cover member 63 is prepared that has a function similar to that of the fixation cover member 60 provided in the decontamination station 9. As with the fixation cover member 60, the cover member 63 is formed to be a tubular body having a bottom. On the inner peripheral surface of an opening end 63A, an annular tube 64A of annular tube seal means 64, which is similar to the annular tube seal means 61, is implanted. A handle 65 is provided on the external side. In a state where an external opening end 16C is covered with the cover member 63, the annular tube 64A is inflated, thereby allowing the external opening end 16C of the connector 16 to be sealed from the outside. Gas with which the annular tube 64A is inflated can be supplied from the manual operation module 7 through hose 66.

A method of decontaminating the isolator system according to the present invention is described.

When the inside of the main isolator 3 is decontaminated, in a state where the connection between the connection ports 13 and 14 and the connectors 15 and 16 are disengaged, the small connection ports 13 are equipped with the small blocking members 30A as shown in FIG. 3(A) and the annular tube 19A of the annular tube seal means 19 is inflated to seal the outer opening end 13C, while the large connection port 14 is equipped with the blocking member 30B as shown in FIG. 4(A) and the annular tube 19A of the annular tube seal means 19 is inflated to seal the outer opening end 14C. Subsequently, as shown in FIGS. 3(C) and 4(B), in the main isolator 3, the inner opening/closing mechanisms 20 and 26 are actuated to separate the closing members 21 and 27 from the inner opening ends 13A and 14A of the connection ports 13 and 14.

In this state, the decontamination means 35 is actuated to supply hydrogen peroxide vapor as the decontamination medium into the main isolator 3 from the supply and exhaust source 36 and to circulate the medium, thereby decontaminating the entire inside of the main isolator 3. In this case, the outer peripheral surface 21A and an outer peripheral surface 27A of the closing members 21 and 27 and covered spots including sealed portions, such as the annular tubes 18A implanted in the inner peripheral surfaces of the inner opening ends 13A and 14A, which are not exposed and have been incapable of being decontaminated in the state where the inner opening ends 13A and 14A of the connection ports 13 and 14 are closed with the closing members 21 and 27 as shown in FIGS. 3(A) and 4(A), can be decontaminated. Contact with the decontamination medium is maintained for a predetermined time defined in validation. Subsequently, aseptic air is supplied from the supply and exhaust source 36 and circulated. Aeration is performed for the predetermined time to remove the decontamination component, and a decontamination operation is completed.

In cases of decontaminating the insides of the small incubators 4 and the large incubator 5, in a state where the connection between the connection ports 13 and the connectors 15 is disengaged, as shown in FIG. 1, the small incubators 4 and the large incubator 5 are connected to the decontamination station 9 sequentially one by one, and hydrogen peroxide vapor as the decontamination medium is supplied from the decontamination station 9.

To connect the incubators 4, 5 to the decontamination station 9, the corresponding front surfaces 4A, 5A of the incubator 4, 5 is caused to approach the front surface 9A of the decontamination station 9 to have a distance that allows the L-shaped movable hook 53A of the positioning mechanism 50 to be engaged with the L-shaped fitting 56. In this state, the retracting means 53 is actuated. Thus, one of the connectors 15 of the incubators 4, 5 is fitted to the fixation cover member 60 of the decontamination station 9, and the supply and exhaust pipe 62 of the decontamination station 9 is connected to the connection pipe 41 of the incubators 4, 5. When this state is achieved, the annular tube 61A of the annular tube seal means 61 implanted in the inner peripheral surface of the fixation cover member 60 is inflated to seal an external opening end 15C of the connector 15 of the incubators 4, 5, and the rotation drive means 45 of the inner closing mechanism 43 is actuated to open the lid member 44.

In this state, the butterfly valve in the connection pipe 41 is opened, hydrogen peroxide vapor as the decontamination medium is supplied from the supply and exhaust pipe 62 and circulated to decontaminate the entire inside of the incubators 4, 5. In this case, the covered spots including sealed portions, such as the outer side of the lid member 44 and the seal member 46, which are not exposed and have been incapable of being decontaminated in a state where the lid member 44 is closed, can be decontaminated.

Contact with the decontamination medium is maintained for a predetermined time defined in validation. Subsequently, aseptic air is supplied from the supply and exhaust pipe 62 and circulated. Aeration is performed for a predetermined time to remove the decontamination component, and the decontamination operation is completed.

The material introduction module 6 is decontaminated in a state of being connected to the manual operation module 7. In this case, in a state where the connection between the connection port 14 and the connector 16 is disengaged, the connector 16 of one side surface 6C of the material introduction module 6 is connected to the connection port 17 of the manual operation module 7 as shown in FIG. 6(A), while the external opening end 16C of the connector 16 on the other side surface 6B is sealed with the cover member 63 as shown in FIG. 6(B). In this state, the closing member 27 of the manual operation module 7 and the fitting lid member 49 on the side surfaces 6B and 6C of the material introduction module 6 are opened, the decontamination means 35 is actuated in a state where a communication portion (not shown) for communication with the pass box 8 is opened, hydrogen peroxide vapor as the decontamination medium is supplied from the supply and exhaust source 36 into the manual operation module 7 and circulated, and the entire inner regions of the manual operation module 7, the material introduction module 6 and the pass box 8 are decontaminated. In this case, the covered spots, including sealed portions such as the outer peripheral surface 27A of the closing member 27, the annular tube 18A, the outer peripheral surface 49A of the fitting lid member 49 and the annular tube 47A, which are not exposed and have been incapable of being decontaminated in a state where the closing member 27 and the fitting lid member 49 are closed, can be decontaminated.

Contact with the decontamination medium is maintained for a predetermined time defined in validation. Subsequently, aseptic air is supplied from the supply and exhaust source 36 and circulated. Aeration is performed for a predetermined time to remove the decontamination component, and decontamination is completed.

Lastly, a method of using the isolator system 1 of the present invention that has the aforementioned configuration is described.

In a state of use where the inner decontamination has been completed, the main isolator 3 is in a state where the inner opening end 13A of the small connection port 13 is closed with the closing member 21 and is sealed with the annular tube seal means 18, and the outer opening end 13C is equipped with the small blocking member 30A, while the annular tube 19A of the annular tube seal means 19 is deflated to release the blockage. Likewise, the inner opening end 14A of the large connection port 14 is also closed with the closing member 27 and is sealed with the annular tube seal means 18, and the outer opening end 14C is equipped with the large blocking member 30B, while the annular tube 19A of the annular tube seal means 19 is deflated to release the blockage.

As to the small incubator 4, in a state where the inner opening end 15B of the connector 15 is sealed with the lid member 44, the blockage of the external opening end 15C with the fixation cover member 60 is released, this incubator is moved from the decontamination station 9 to the culture station 10, is joined by the positioning mechanism 50 and is on standby. In this state, the utility connector 57 of the culture station 10 is connected with the connection target 58 of the incubator 4, the power and required air are supplied, thus maintaining the inner space for accommodating the cells to be in an aseptic state and in an environment suitable for culturing. Meanwhile, in the case of the large incubator 5, this incubator is connected to the decontamination station 9 and decontamination is completed, and subsequently, in a state where the inner opening end 15B of the connector 15 is sealed with the lid member 44, the annular tube 61A of the annular tube seal means 61 provided for the fixation cover member 60 is deflated to release the blockage. In this state, the utility connector 57 of the decontamination station 9 is connected with the connection target 58 of the incubator 5, the power and required air are supplied, thus maintaining the inner space for accommodating the cells to be in an aseptic state and in an environment suitable to culture.

Furthermore, the material introduction module 6 is in a state of being connected to the manual operation module 7. The connector 16, which is provided on the side surface 6B and is to be connected to the large connection port 14 of the main isolator 3, is in a state where the inner opening end 16B is sealed with the fitting lid member 49. The external opening end 16C is equipped with the cover member 63. Meanwhile, the annular tube 64A of the annular tube seal means 64 is deflated. Meanwhile, the connector 16 provided on the side surface 6C is maintained to be in a state where the annular tube 19A of the annular tube seal means 19 of the large connection port 17 of the manual operation module 7 is inflated. The inner opening end 16B and an inner opening end 17A are each maintained in the open state in decontamination.

In the aforementioned state after decontamination, the operator introduces cells and culture instruments, such as a culture vessel, for operation. To introduce these items, first, the cells and culture instruments brought into the operation room 2 are decontaminated or sterilized on their outer surfaces in the pass box 8, and then are conveyed into the manual operation module 7. In the manual operation module 7, the operator removes the exteriors of the culture instrument through the glove G from the outside, and the cells and culture instruments are accommodated in the material introduction module 6.

After the items, such as materials, are accommodated in the material introduction module 6, the inner opening/closing mechanism 26 is actuated to seal the inner opening end 17A of the connection port 17 of the manual operation module 7 with the closing member 27 and to seal this opening end with the annular tube seal means 18, while the inner closing mechanism 48 of the material introduction module 6 is actuated to seal the inner opening end 16B of the connector 16 with the fitting lid member 49 and to seal this opening end with the annular tube seal means 47. In this state, the annular tube 19A on the outer opening end 17C side of the connection port 17 is deflated. Furthermore, the retracting means 53 of the positioning mechanism 50 is actuated to disengage the fitting state between the L-shaped movable hook 53A on the manual operation module 7 side and the L-shaped fitting 56 on the material introduction module 6 side. After this state is achieved, the operator moves the material introduction module 6 to connect this module to the main isolator 3.

The main isolator 3 is joined at the side surface 3C with the material introduction module 6 by the positioning mechanism 50. The large connection port 14 is connected with the large connector 16. To the side surface 3B, the small incubator 4 or the large incubator 5 is moved and joined thereto by the positioning mechanism 50. The small connection port 13 is connected with the small connector 15.

The blocking member 30B is removed from the large connection port 14. Subsequently, as shown in FIG. 6(A), the pipe-shaped member 16A of the connector 16 is fitted to the inside of the tubular member 14B of the connection port 14. While the sealed states of the inner opening end 14A and the inner opening end 16B are maintained, the annular tube 19A on the outer opening end 14C side of the connection port 14 is inflated to seal the gap. Thus, a state of allowing communication where the inflow of the external atmosphere and the outflow of internal atmosphere are blocked is achieved. In this state, the decontamination means 35 is actuated to supply hydrogen peroxide vapor from the supply and exhaust source 36 through the supply pipe 37 to the inner hollow space formed by the tubular member 14B of the connection port 14 and the pipe-shaped member 16A of the connector 16 and to exhaust the vapor through the exhaust pipe 38, thus circulating the vapor. After the hydrogen peroxide vapor has been circulated for a predetermined time, the supply of the hydrogen peroxide vapor is stopped, aseptic air is supplied from the supply and exhaust source 36 to circulate the air, and aeration is performed for a predetermined time. Through the decontamination operation in conformity with such a validation, spots are decontaminated which include the inner peripheral surfaces of the tubular member 14B and the pipe-shaped member 16A and the outer surfaces of the closing member 27 and the fitting lid member 49, which are exposed to the external atmosphere in the operation room 2. After the decontamination is completed, both the closing member 27 and the fitting lid member 49 are opened to cause the inside of the material introduction module 6 and the inside of the main isolator 3 to communicate with each other.

Figure 5B:
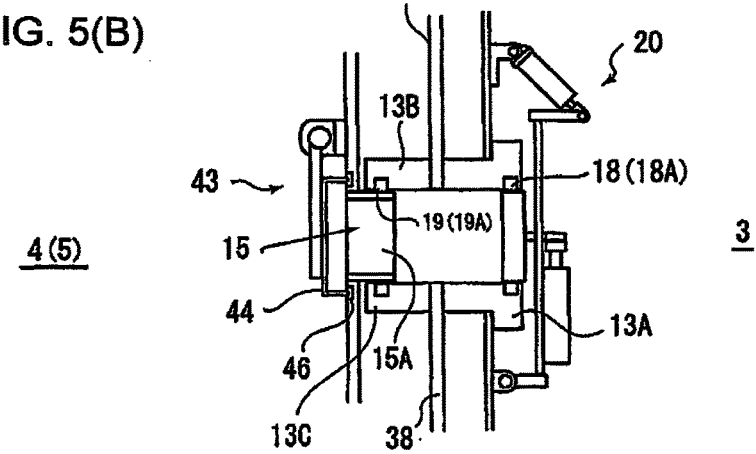
Figure 5C:
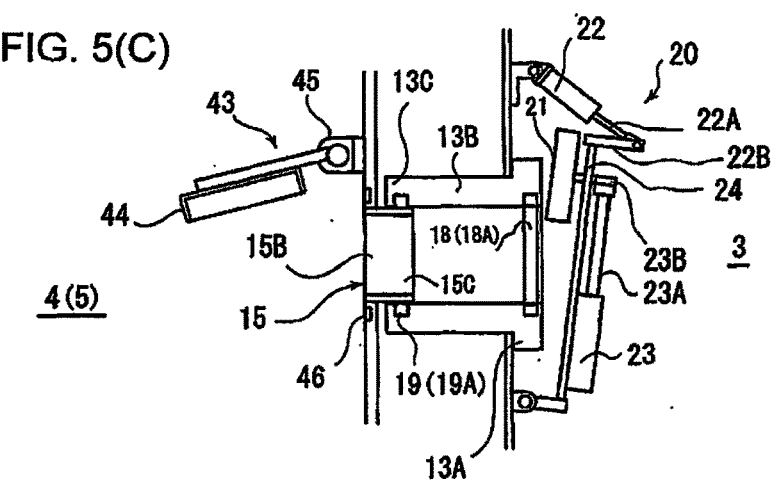

The blocking member 30A is removed from the small connection port 13. Subsequently, as shown in FIG. 5b, the pipe-shaped member 15A of the connector 15 is fitted to the inside of the tubular member 13B of the connection port 13. While the sealed states of the inner opening end 13A and the inner opening end 15B are maintained, the annular tube 19A on the outer opening end 13C side of the connection port 13 is inflated to seal the gap. Thus, a state of allowing communication where the inflow of the external atmosphere and the outflow of internal atmosphere are blocked is achieved. In this state, the decontamination means 35 is actuated to supply hydrogen peroxide vapor from the supply and exhaust source 36 through the supply pipe 37 to the inner hollow space formed by the tubular member 13B of the connection port 13 and the pipe-shaped member 15A of the connector 15 and to exhaust the vapor through the exhaust pipe 38, thus circulating the vapor. After the hydrogen peroxide vapor has been circulated for a predetermined time, the supply of the hydrogen peroxide vapor is stopped, the aseptic air is supplied from the supply and exhaust source 36, and aeration is performed for a predetermined time. Through the decontamination operation in conformity with such a validation, spots are decontaminated which include the inner surfaces of the tubular member 13B and the pipe-shaped member 15A and the outer surfaces of the closing member 21 and the lid member 44, which are exposed to the external atmosphere in the operation room 2. After the decontamination is completed, both the closing member 21 and the lid member 44 are opened to cause the inside of the main isolator 3 and the inside of the incubators 4, 5 to communicate with each other.

When this state is achieved, the robot R in the main isolator 3 is actuated to introduce the cells and culture instruments into the main isolator 3, perform an operation of seeding cells in the culture vessel, and cause the incubators 4, 5 to accommodate the culture vessel in which the cells are seeded. To disengage the connection state between the connection port 13 and the connector 15, as shown in FIG. 5(B), the inner opening end 13A and the inner opening end 15B are closed with the closing member 21 and the lid member 44, respectively. Subsequently, the annular tube 19A of the annular tube seal means 19 is deflated, the joining state by the positioning mechanism 50 is disengaged, and the incubators 4, 5 are moved. The small incubator 4 that accommodates the cells is connected to the culture station 10, and culturing is performed for a predetermined period. In a case where the cells are accommodated in the large incubator 5, this incubator is connected to the decontamination station 9, and culturing is performed for a predetermined period.

After the predetermined culturing period has elapsed, the incubators 4, 5 are reconnected to the main isolator 3, the cells are transferred into the main isolator 3, culture conversion or passage operation is performed, the cells are accommodated in the incubators 4, 5 again, and culturing is performed for a predetermined period. Alternatively, when all the culturing steps are finished, the cultured cells are accommodated in the connected material introduction module 6, and the cells are conveyed from the isolator system 1 through the manual operation module 7 and the pass box 8 to the operation room 2.

In the above description, the case is thus described where the tubular members 13B, 14B and 17B are configured as the outer tubular members, and the pipe-shaped members 15A and 16A are configured as the inner tubular members. The configuration is not limited thereto. As to the tubular member constituting the connection means, the inside and the outside can be configured in an inverted manner. The annular tube seal means 19 to seal the gap may be provided for any or both of the inside and the outside, or multiple pieces of the seal means may be provided. Accordingly, as to the fitting states of the blocking member 30 (30A, 30B), the fixation cover member 60, and the cover member 63, the insides and the outsides can be configured in an inverted manner.

What is claimed is:

1. A method of decontaminating an isolator system including a main isolator in which an aseptic operation is performed, and a subisolator connectable to the main isolator, comprising the steps of:

when decontaminating an inside of the main isolator, disengaging a connection between a first opening connector formed at the main isolator and a second opening connector formed at the subisolator, blocking the first opening connector with a first blocking member provided outside the main isolator at an outside of the first opening connector, opening a first opening/closing member which opens and closes the first opening connector in the main isolator, and supplying a decontamination medium into the main isolator to perform decontamination in this state to decontaminate a covered spot which is not exposed when the first opening/closing member is closed;

when decontaminating an inside of the subisolator, disengaging a connection between the first opening connector and the second opening connector, blocking the second opening connector with a second blocking member provided outside the subisolator at an outside of the second opening connector, opening a second opening/closing member which opens and closes the second opening connector in the subisolator, and supplying the decontamination medium into the subisolator to perform decontamination in this state to decontaminate a covered spot which is not exposed when the second opening/closing member is closed; and when decontaminating the insides of the main isolator and the subisolator, closing the first opening/closing member and the second opening/closing member, subsequently releasing blockage by the first blocking member and the second blocking member, connecting the first opening connector and the second opening connector to each other, bringing the inside of the main isolator and the inside of the subisolator into a state of allowing communication with each other with inflow of an external atmosphere being blocked, supplying the decontamination medium to decontaminate a spot exposed to an external atmosphere when the blockage by the first blocking member and the second blocking member is released, and opening the first opening/closing member and the second opening/closing member to cause the insides of the main isolator and the subisolator to communicate with each other via the first opening connector and the second opening connector.

* * * * *